United States Patent
He et al.

(10) Patent No.: US 11,952,400 B2
(45) Date of Patent: Apr. 9, 2024

(54) BOVINE ROTAVIRUS FUSION PROTEIN AND CALF DIARRHEA MULTIVALENT VACCINE

(71) Applicant: TECON BIOPHARMACEUTICAL CO., LTD., Xinjiang (CN)

(72) Inventors: Sun He, Xinjiang (CN); Yiping Pan, Xinjiang (CN); Guoqing Zhang, Xinjiang (CN); Pengxian Yan, Xinjiang (CN); Na Xi, Xinjiang (CN); Miaomiao Guo, Xinjiang (CN); Shengdong Xiao, Xinjiang (CN); Tianzeng Li, Xinjiang (CN); Rui Han, Xinjiang (CN); Yumeng Wang, Xinjiang (CN); Jiubin Du, Xinjiang (CN); Pei Zheng, Xinjiang (CN); Jian Cao, Xinjiang (CN)

(73) Assignee: TECON BIOPHARMACEUTICAL CO., LTD., Xinjiang (CN)

( * ) Notice: Subject to any disclaimer, the term of this patent is extended or adjusted under 35 U.S.C. 154(b) by 246 days.

(21) Appl. No.: 17/232,952

(22) Filed: Apr. 16, 2021

(65) Prior Publication Data
US 2022/0002350 A1    Jan. 6, 2022

(30) Foreign Application Priority Data
Jul. 6, 2020    (CN) .......................... 202010638005.2

(51) Int. Cl.
| | |
|---|---|
| *C07K 14/005* | (2006.01) |
| *A61K 39/108* | (2006.01) |
| *A61K 39/15* | (2006.01) |
| *C07K 14/245* | (2006.01) |
| *C12N 7/00* | (2006.01) |
| *A61K 39/00* | (2006.01) |

(52) U.S. Cl.
CPC ........ *C07K 14/005* (2013.01); *A61K 39/0258* (2013.01); *A61K 39/15* (2013.01); *C07K 14/245* (2013.01); *C12N 7/00* (2013.01); *A61K 2039/5258* (2013.01); *A61K 2039/552* (2013.01); *A61K 2039/70* (2013.01); *C07K 2319/40* (2013.01); *C12N 2720/12322* (2013.01); *C12N 2720/12323* (2013.01); *C12N 2720/12334* (2013.01); *C12N 2720/12352* (2013.01); *C12N 2770/20022* (2013.01); *C12N 2770/20023* (2013.01); *C12N 2770/20034* (2013.01); *C12N 2770/20052* (2013.01)

(58) Field of Classification Search
None
See application file for complete search history.

(56) References Cited

U.S. PATENT DOCUMENTS

2016/0185826 A1*  6/2016  Lin .......................... C12N 7/00
                                                                    435/235.1

OTHER PUBLICATIONS

Gonzalez DD, et al. Evaluation of a bovine rotavirus VP6 vaccine efficacy in the calf model of infection and disease. Vet Immunol Immunopathol. Sep. 15, 2010;137(1-2):155-60. doi: 10.1016/j.vetimm.2010.04.015. Epub Apr. 29, 2010. PMID: 20546933. 2010.*

* cited by examiner

*Primary Examiner* — Benjamin P Blumel
*Assistant Examiner* — Jeffrey Mark Sifford
(74) *Attorney, Agent, or Firm* — Perry + Currier Inc.

(57) ABSTRACT

Provided are a bovine rotavirus fusion protein and calf diarrhea multivalent vaccine. The bovine rotavirus fusion protein contains a VP6 fragment, wherein the VP6 fragment contains an amino acid sequence as represented by SEQ ID NO. 4, and at least one loop region of the following (a)~(c) is substituted with an antigenic epitope derived from bovine coronavirus and/or an antigenic epitope derived from *E. coli*: (a) amino acid residues of sites 168-177; with an amino acid sequence as represented by SEQ ID NO. 1; (b) amino acid residues of sites 194-205; with an amino acid sequence as represented by SEQ ID NO. 2; and (a) amino acid residues of sites 296-316, with an amino acid sequence as represented by SEQ ID NO. 3, The bovine rotavirus fusion protein contains a plurality of antigenic epitopes, and can enable a host to generate a plurality of antibodies after immunizing the host.

8 Claims, 5 Drawing Sheets
Specification includes a Sequence Listing.

BOVINE ROTAVIRUS FUSION PROTEIN AND CALF DIARRHEA MULTIVALENT VACCINE

CROSS-REFERENCE TO RELATED APPLICATION

This application claims priority to Chinese Patent Application No. 2020106380052, filed with the Chinese Patent Office on Jul. 6, 2020, entitled "Bovine Rotavirus Fusion Protein and Calf Diarrhea Multivalent Vaccine", which is incorporated herein by reference in its entirety.

SEQUENCE LISTING

This disclosure references a Sequence Listing submitted as an ASCII text file, entitled "17232952 SEQ LISTING" originally created on Apr. 16, 2021 and revised on Jun. 25, 2021, having a size of 27 KB, the contents of which is incorporated herein by reference in its entirety.

TECHNICAL FIELD

The present disclosure relates to the technical field of molecular biology, in particular to a bovine rotavirus fusion protein and calf diarrhea multivalent vaccine.

BACKGROUND ART

The calf diarrhea, as one of the most common clinical diseases in a cattle farm, is common to calves of 7-15 days, has high morbidity and mortality, thus not only causing significant economic loss to the cattle farm, but also affecting the growth and development of the calves and the lactation performance in adulthood. Among the pathogenic factors, bovine rotavirus (BRV), bovine coronavirus and toxigenic E. coli are three main pathogens that cause the calf diarrhea, wherein BRV caused calf diarrhea has the highest incidence, accounting for about 46% of calf diarrhea cases.

After bovine rotavirus infection, the clinical characteristics are lethargy, anorexia, vomiting, diarrhea and dehydration, and weight loss. The bovine coronavirus is one of the other main pathogens that cause newborn calf diarrhea, clinically mainly characterized by hemorrhagic diarrhea, depression of sick cattle, reduction or stopping of milk intake, serious features such as fever, dehydration, blood concentration, and death may occur in a few cattle. Bovine colibacillosis is an infectious disease caused by pathogenic E. coli, and mainly affects calves. When the newborn calves have insufficient resistance or digestive disorder, they may be attacked. The incubation period of disease for calf is very short, the sick cattle often appear in the forms of diarrhea, septicemia and the like, the body temperature may rise to 40° C., and symptoms such as pneumonia and arthritis appear when the course of disease is prolonged. Calf diarrhea caused by pathogenic E. coli may occur all the year round, and is mostly caused in the period of drylot feeding in winter and spring. The disease is in locally endemic or sporadic form when attacking to the bovine, and great harm is brought to the breeding industry all over the world.

The calf diarrhea has the problem of cross infection, the rotavirus infection facilitates attachment and mixed infection of other pathogens such as pathogenic E. coli, then the calf diarrhea is more severe, the mortality is higher, and when there is mixed infection of coronavirus, the condition is more severe, and the mortality of the sick calves can be as high as 50%-100%. Due to the existence of reasons of cross infection and repeated attack of diarrhea, pathogens are extremely difficult to purify, and vaccine immunization becomes an important means for preventing and treating calf diarrhea. At present, no commercial mature vaccine capable of preventing and controlling calf diarrhea caused by a variety of pathogens exists in the market.

In view of this, the present disclosure is specifically proposed.

SUMMARY

According to one aspect of the present disclosure, the present disclosure provides a bovine rotavirus fusion protein, which contains a VP6 fragment, wherein the VP6 fragment contains an amino acid sequence as represented by SEQ ID NO: 4, and at least one loop region of the following (a)~(c) in the amino acid sequence as represented by SEQ ID NO: 4 is substituted with a fragment of an antigenic epitope derived from bovine coronavirus and/or an antigenic epitope derived from E. coli:

(a) amino acid residues of sites 168-177, with an amino acid sequence as represented by SEQ ID NO: 1;
(b) amino acid residues of sites 194-205, with an amino acid sequence as represented by SEQ ID NO: 2; and
(c) amino acid residues of sites 296-316, with an amino acid sequence as represented by SEQ ID NO: 3.

According to one aspect of the present disclosure, the present disclosure provides a nucleic acid encoding the bovine rotavirus fusion protein.

According to one aspect of the present disclosure, the present disclosure provides a virus-like particle assembled from the bovine rotavirus fusion protein.

According to one aspect of the present disclosure, the present disclosure provides a method for preparing the virus-like particle, including expressing genes encoding the bovine rotavirus fusion protein in a host.

According to one aspect of the present disclosure, the present disclosure provides a host expressing the bovine rotavirus fusion protein or the virus-like particle.

According to one aspect of the present disclosure, the present disclosure provides calf diarrhea multivalent vaccine, which contains the bovine rotavirus fusion protein, the nucleic acid or the virus-like particles.

BRIEF DESCRIPTION OF DRAWINGS

In order to more clearly illustrate technical solutions in the embodiments of the present disclosure or the prior art, accompanying drawings which need to be used in the description of the embodiments or the prior art will be introduced briefly below. Apparently, the accompanying drawings in the description below are for some embodiments of the present disclosure. A person ordinarily skilled in the art still could obtain other accompanying drawings in light of these accompanying drawings, without using creative efforts.

DETAILED DESCRIPTION OF EMBODIMENTS

Figure 1:
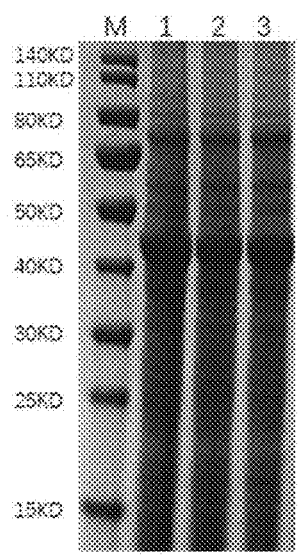
FIG. 1 shows SDS-PAGE detection result of VP6-S-K88/K99 fusion protein prepared in Example 1 of the present disclosure.

Technical solutions of the present disclosure will be described below clearly and comprehensively in connection with examples. Apparently, the described examples are only a part of examples of the present disclosure, rather than all examples. All of other examples, obtained by those ordinarily skilled in the art based on the examples in the present disclosure without using any creative efforts, shall fall into the scope of protection of the present disclosure.

A first objective of the present disclosure is to provide a bovine rotavirus fusion protein, which contains a plurality of antigenic epitopes, and can enable a host to generate a plurality of antibodies after immunizing the host.

A second objective of the present disclosure is to provide a virus-like particle assembled from the above bovine rotavirus fusion protein.

A third objective of the present disclosure is to provide calf diarrhea multivalent vaccine.

In order to solve the above technical problems, the present disclosure specifically adopts following technical solutions.

According to one aspect of the present disclosure, the present disclosure provides a bovine rotavirus fusion protein, which contains a VP6 fragment, wherein the VP6 fragment contains an amino acid sequence as represented by SEQ ID NO: 4, and at least one loop region of the following (a)~(c) in the amino acid sequence as represented by SEQ ID NO: 4 is substituted with a fragment of an antigenic epitope derived from bovine coronavirus and/or an antigenic epitope derived from *E. coli*:

(a) amino acid residues of sites 168-177, with an amino acid sequence as represented by SEQ ID NO: 1;
(b) amino acid residues of sites 194-205, with an amino acid sequence as represented by SEQ ID NO: 2; and
(c) amino acid residues of sites 296-316, with an amino acid sequence as represented by SEQ ID NO: 3.

Preferably, in the VP6 fragment, at least one loop region in (a)~(c) is substituted with at least one antigenic epitope in (d)~(f) below:

(d) a coronavirus antigenic epitope having an amino acid sequence as represented by SEQ ID NO: 5 and/or SEQ ID NO: 11;
(e) an *E. coli* K88 antigenic epitope having an amino acid sequence as represented by SEQ ID NO: 6; and
(f) an *E. coli* K99 antigenic epitope having an amino acid sequence as represented by SEQ ID NO: 7.

Preferably, the amino acid sequence of the VP6 fragment is represented by SEQ ID NO: 8 and/or SEQ ID NO: 13.

Preferably, the bovine rotavirus fusion protein further contains at least one of a VP2 fragment, a VP4 fragment and a VP7 fragment;

Preferably, the bovine rotavirus fusion protein contains the VP6 fragment and the VP2 fragment.

According to one aspect of the present disclosure, the present disclosure provides a nucleic acid encoding the bovine rotavirus fusion protein.

Preferably, a nucleotide sequence encoding the VP6 fragment is represented by SEQ ID NO: 9 or SEQ ID NO: 15.

According to one aspect of the present disclosure, the present disclosure provides a virus-like particle assembled from the bovine rotavirus fusion protein.

According to one aspect of the present disclosure, the present disclosure provides a method for preparing the virus-like particle, including expressing genes encoding the bovine rotavirus fusion protein in a host;

preferably, the host includes *E. coli*, yeast, insect cells, plant or mammalian cells, preferably including yeast;
preferably, the host includes monoclonals obtained after screened by selection pressure;
preferably, genes encoding a part of the bovine rotavirus fusion protein are first introduced into the host, to screen out highly expressed monoclonals, and then genes encoding the remaining part of the bovine rotavirus fusion protein are introduced; and
preferably, the method includes inducing the host to express the bovine rotavirus fusion protein, lysing the host to extract supernatant, and then purifying the supernatant using an ammonium sulfate precipitation method and a chromatography method to obtain virus-like particles.

According to one aspect of the present disclosure, the present disclosure provides a host expressing the bovine rotavirus fusion protein or the virus-like particle.

According to one aspect of the present disclosure, the present disclosure provides calf diarrhea multivalent vaccine, which contains the bovine rotavirus fusion protein, the nucleic acid or the virus-like particles;

preferably, the calf diarrhea multivalent vaccine includes the virus-like particles and adjuvant, wherein the adjuvant preferably includes ISA206 adjuvant.

Compared with the prior art, the present disclosure has the following beneficial effects:

by substituting the loop region of the VP6 fragment with the fragment of the antigenic epitope derived from the bovine coronavirus and/or the antigenic epitope derived from the *E. coli*, the bovine rotavirus fusion protein provided in the present disclosure is enabled to contain not only the bovine rotavirus antigen, but also at least one of the bovine coronavirus antigen and the antigen of *E. coli*, and can enable animals to generate relatively strong immune protection against various pathogens after immunizing the animals as an immunogen, thus having the application value for preparing the multivalent vaccine.

The virus-like particles provided in the present disclosure are formed after soluble expression of the genes encoding the bovine rotavirus fusion protein using the exogenous expression system through the genetic engineering technology, displays the main antigenic epitopes of the bovine coronavirus and/or the *E. coli* on the surfaces of the chimeric virus-like particles, has quite good immunogenicity against the bovine rotavirus, the bovine coronavirus and/or the pathogenic *E. coli*. After the virus-like particles are used as immunogen to immunize animals, the animals can generate relatively strong immune protection against the various pathogens.

The calf diarrhea multivalent vaccine provided in the present disclosure chimerizes antigens derived from a plurality of pathogens and capable of inducing organisms to produce specific antibodies, thereby expanding the preventing and controlling scope for disease, saving the labor, and improving the working efficiency. Moreover, the calf diarrhea multivalent vaccine is multivalent subunit vaccine prepared using the genetic engineering technology, has the characteristics such as no toxin dispersion and no toxicity increasing, may be used for pregnant cows and newborn calves, can be quickly served to the market, and has wide application prospects.

According to one aspect of the present disclosure, the present disclosure provides a bovine rotavirus fusion protein, which contains a VP6 fragment, wherein the VP6 fragment contains an amino acid sequence as represented by SEQ ID NO: 4, and at least one loop region of the following (a)~(c) in the amino acid sequence as represented by SEQ ID NO: 4 is substituted with a fragment of an antigenic epitope derived from bovine coronavirus and/or an antigenic epitope derived from *E. coli*:
  (a) amino acid residues of sites 168-177, with an amino acid sequence as represented by SEQ ID NO: 1;
  (b) amino acid residues of sites 194-205, with an amino acid sequence as represented by SEQ ID NO: 2; and
  (c) amino acid residues of sites 296-316, with an amino acid sequence as represented by SEQ ID NO: 3.

The rotavirus belongs to rotavirus genus of reoviridae, an outer capsid of the virus particles is composed of two layers, i.e. glycoproteins VP7 and VP4, and a middle layer is composed of VP6, where a main antigenic epitope region exists on VP6 protein, and can trigger neutralizing antibody activity. The VP6 protein determines the genotype of the virus, and is highly conserved among different species, and is the main antigen in rotavirus vaccine research and development. The bovine coronavirus is spherical virus particles with a diameter of about 80-120 nm and belonging to the coronavirus of Coronaviridae, the virus particles are externally wrapped with an aliphatic membrane, and spike protein (S) in three kinds of glycoproteins on the surface of the membrane is a main receptor binding site and a main antigen site. Pathogenic *E. coli* constitutes a variety of serotypes by 173 thallus (0) antigens, 80 surface (K) antigens and 56 flagella (H) antigens, wherein the most common serotypes are K88 and K99. The bovine rotavirus fusion protein provided in the present disclosure contains the bovine rotavirus antigen, the bovine coronavirus antigen and/or the antigen of *E. coli*, and enables animals to generate relatively strong immune protection against various pathogens after immunizing the animals as an immunogen, thus having the application value for preparing the multivalent vaccine.

It should be noted that the antigenic epitopes derived from the same kind of pathogen may include a plurality of antigenic epitopes, and specific examples include, but are not limited to, antigenic epitopes located in different proteins or domains in the same pathogen and having different sequences; or homologous identical antigenic epitopes of the same pathogen but different subtypes; or antigenic epitopes of the same pathogen but located in different proteins or domains in different subtypes, with different sequences. For example, antigenic epitopes derived from *E. coli* include K88 antigenic epitopes and K99 antigenic epitopes derived from main B cell epitope of pathogenic *E. coli*. At least one loop region of (a)~(c) is substituted with other antigenic epitopes, and specific examples include, but are not limited to, that one of (a), (b) or (c) is substituted; (a) and (b) are substituted; (c) and (b) are substituted; (a) and (c) are substituted; or (a), (b) and (c) are all substituted and so on. Antigenic epitopes for substituting different loop regions may be the same or different, and specific examples include, but are not limited to, that all of (a), (b) and (c) are substituted with an antigenic epitope derived from bovine coronavirus or an antigenic epitope derived from *E. coli*; or (a) and (b) are substituted with an antigenic epitope derived from *E. coli*, and (c) is substituted with an antigenic epitope derived from bovine coronavirus.

In some preferred embodiments, in the VP6 fragment of the bovine rotavirus fusion protein, at least one loop region of (a)~(c) is substituted with at least one antigenic epitope in (d)~(f) below;
  (d) a coronavirus antigenic epitope having an amino acid sequence as represented by SEQ ID NO: 5 and/or SEQ ID NO: 11;
  (e) an *E. coli* K88 antigenic epitope having an amino acid sequence as represented by SEQ ID NO: 6; and
  (f) an *E. coli* K99 antigenic epitope having an amino acid sequence as represented by SEQ ID NO: 7.

In some optional embodiments, in the VP6 fragment, the amino acid residues of sites 168-177 of the VP6 fragment are substituted with an antigenic epitope of the *E. coli* K88 having an amino acid sequence represented by SEQ ID NO: 6; the amino acid residues of sites 194-205 of the VP6 fragment are substituted with an antigenic epitope of the *E. coli* K99 having an amino acid sequence represented by SEQ ID NO: 7; and the amino acid residues of sites 296-316 of the VP6 fragment are substituted with a coronavirus antigenic epitope having an amino acid sequence represented by SEQ ID NO: 5. The amino acid sequence of the VP6 fragment obtained after the substitution is represented by SEQ ID NO: 8.

In some optional embodiments, the amino acid residues of sites 168-177 of the VP6 fragment are substituted with an antigenic epitope of the *E. coli* K99 having an amino acid sequence represented by SEQ ID NO: 7; the amino acid residues of sites 194-205 of the VP6 fragment are substituted with an antigenic epitope of the *E. coli* K88 having an amino acid sequence represented by SEQ ID NO: 6; and the amino acid residues of sites 296-316 of the VP6 fragment are substituted with a coronavirus antigenic epitope having an amino acid sequence represented by SEQ ID NO: 11. The amino acid sequence of the VP6 fragment obtained after the substitution is represented by SEQ ID NO: 13.

In some preferred embodiments, the bovine rotavirus fusion protein further may contain at least one of a VP2 fragment, a VP4 fragment and a VP7 fragment, and the bovine rotavirus fusion protein preferably consists of the VP6 fragment and the VP2 fragment.

According to another aspect of the present disclosure, the present disclosure further provides a nucleic acid encoding the above bovine rotavirus fusion protein. In the above, "nucleic acid" refers to a polymeric form of nucleotide with any length, wherein the nucleotide includes ribonucleotides and/or deoxyribonucleotides. Examples of nucleic acid include, but are not limited to, single-stranded, double-stranded or multi-stranded DNA or RNA, genomic DNA, cDNA, DNA-RNA hybrids or polymers containing purine and pyrimidine bases or other natural, chemical or biochemical modifications, non-natural or derived nucleotide bases.

The bovine rotavirus fusion protein provided in the present disclosure may be obtained by expression of a chimeric gene, and also may be obtained by co-expression after introducing a plurality of nucleic acids encoding different regions of the bovine rotavirus fusion protein into the host cell, therefore, the nucleic acid encoding the above bovine rotavirus fusion protein provided in the present disclosure may be an independent nucleic acid molecule containing a chimeric gene, and also may be a set of a plurality of nucleic acid molecules containing independent genes for encoding each part of the bovine rotavirus fusion protein, for example, a set of nucleic acids composed of nucleic acids that encode the VP6 fragment, and encode at least one of the VP2 fragment, VP4 fragment and VP7 fragment, respectively. It may be understood that the nucleic acid may also contain fragments encoding other functional units such as promoters, enhancers, tags and vectors, which are not limited in the present disclosure. Preferably, the nucleic acid encoding the bovine rotavirus fusion protein is subjected to codon optimization, and the nucleic acid sequence encoding the VP6 protein fragment part in the nucleic acid is preferably represented by SEQ ID NO: 9, and it encodes the VP6 fragment having an amino acid sequence represented by SEQ ID NO: 8; or the nucleic acid sequence encoding the VP6 protein fragment part in the nucleic acid is preferably represented by SEQ ID NO: 15, and it encodes the VP6 fragment having an amino acid sequence represented by SEQ ID NO: 13.

According to another aspect of the present disclosure, the present disclosure further provides a virus-like particle assembled from the bovine rotavirus fusion protein. VLP is formed by autonomously assembling one or several structural proteins of virus, and mimic natural viral particles in size, morphology and composition, without viral genome, without infectivity, and having advantages in immunogenicity, antigen stability and production. VLP combines the best advantages of whole viruses and subunit antigens. The chimeric virus-like particles can be formed after soluble expression of the genes encoding the bovine rotavirus fusion protein using the exogenous expression system through the genetic engineering technology, displays the main antigenic epitopes of the bovine coronavirus and/or the *E. coli* on the surfaces of the chimeric virus-like particles, has quite good immunogenicity against the bovine rotavirus, the bovine coronavirus and/or the pathogenic *E. coli*. After the VLP is used as immunogen to immunize animals, the animals can generate relatively strong immune protection against various pathogens.

According to another aspect of the present disclosure, the present disclosure further provides a method for preparing the above virus-like particles, which method includes: expressing genes encoding the bovine rotavirus fusion protein in a host. The genes encoding the bovine rotavirus fusion proteins may be located in the same nucleic acid fragment, and also may be located in different nucleic acid fragments, and the genes located in different nucleic acid fragments are co-expressed in a host, so that the host expresses the virus-like particles. The genes encoding the bovine rotavirus fusion protein preferably are subjected to rare codon optimization firstly.

The host includes *E. coli*, yeast, insect cells, plant or mammalian cells, preferably including yeast. The yeast expression system may be subjected to post-translation modification, such as glycosylation or phosphorylation, meanwhile the expression amount of the target protein is increased, and the production cost is reduced. At the same time, preferably, the host capable of expressing the genes encoding the bovine rotavirus fusion protein is monoclonal after screening under selection pressure, so as to increase the amount of the protein expressed by the host, preferably with high concentration antibiotics as screening pressure. When the genes encoding the bovine rotavirus fusion protein are located in different nucleic acid fragments, genes encoding a part of the bovine rotavirus fusion proteins may be first introduced into the host, to screen out highly expressed monoclonals, and then genes encoding the remaining part of the bovine rotavirus fusion proteins are introduced into the monoclonals, so as to further increase the expression amount of target proteins.

In some optional embodiments, taking the yeast acting as the host cell as an example, the method includes steps of preparing genes, constructing recombinant vector, cell transfection, screening highly expressed strains and obtaining recombinant proteins, specifically including: firstly linearizing the obtained vectors, then subjecting the yeast competent cells to electrotransformation, expressing the fusion protein, and purifying the obtained fusion protein, then, selecting a suitable buffer solution to perform viroid particle assembly on the purified fusion protein, and identifying the assembly effect using an electron microscope. The vectors preferably are pPIC3.5K vectors. After the linearized vectors are subjected to electrotransformation into the yeast competent cells, the yeast competent cells are preferably directly coated on a high antibiotic concentration plate, and highly expressed monoclonal strains are selected using a relatively high selection pressure. The electrotransformation is preferably performed multiple times, that is, on the basis of the first highly expressed strain, the expression vectors containing other part of target protein genes are again integrated.

According to another aspect of the present disclosure, the present disclosure further provides a host expressing the bovine rotavirus fusion protein or expressing the virus-like particles. The host provided in the present disclosure is a recombinant cell or recombinant microorganism obtained by introducing a nucleic acid encoding the bovine rotavirus fusion protein into a host. In some preferred embodiments, the nucleic acid is introduced into the host through a vector, the host preferably includes yeast, and the vector preferably is pPIC3.5K.

According to another aspect of the present disclosure, the present disclosure further provides calf diarrhea multivalent vaccine, which contains the bovine rotavirus fusion protein, the nucleic acid or the virus-like particle encoding the bovine rotavirus fusion protein. The multivalent vaccine prepared by chimerizing a plurality of antigens, i.e. the bovine rotavirus, and the bovine coronavirus and/or the *E. coli* that pathogenically induce organisms to generate specific antibodies expands the disease control range, saves the labor, and improves the working efficiency. Moreover, the calf diarrhea multivalent vaccine is multivalent subunit vaccine prepared using the genetic engineering technology, has the characteristics such as no toxin dispersion and no toxicity increasing, may be used for pregnant cows and newborn calves, can be quickly served to the market, and has wide application prospects.

In some preferred embodiments, the bovine diarrhea multivalent vaccine includes virus-like particles assembled from bovine rotavirus fusion proteins and an adjuvant. The virus-like particles are taken as immunogen, the antigens are highly concentrated, and the chimeric antigenic epitopes have a certain spatial structure, and have a better immune effect. The adjuvant may be a conventional adjuvant in the art, which is not limited in the present disclosure, and the ISA206 adjuvant is preferably used.

The technical solutions and beneficial effects of the present disclosure are further described below in connection with preferred examples.

Example 1

Expression of Fusion Protein by *Pichia pastoris* Expression System:

the bovine rotavirus VP6 protein structure was analyzed by means of structural biology, and the antigenic epitopes of the bovine coronavirus and pathogenic *E. coli* were embedded onto the bovine rotavirus VP6 protein backbone, with a sequence named VP6-S-K88/K99, and a specific amino acid sequence represented by SEQ ID NO: 8;

the fusion protein VP6-S-K88/K99 was subjected to a *Pichia pastoris* expression system codon optimization, and the nucleotide sequence was represented by SEQ ID NO: 9.

The genes encoding the VP6-S-K88/K99 fusion protein were synthesized by means of genetic engineering, the target genes were inserted into the pPIC3.5k vectors via Bam HI and Age I, and the positive recombinant vectors were screened out through enzymatic identification and sequencing, transformed into *E. Coli* DH5a competent cells for amplification, and the plasmids were extracted in large quantity, named as pPIC3.5K-VP6-S-K88/K99.

After the pPIC3.5K-VP6-S-K88/K99 plasmids were subjected to linearize restriction enzyme digestion with Pme I restriction endonuclease, the linear expression plasmids were recovered, and measured for the purity and concentration thereof.

The competent cells subjected to electrotransformation of *Pichia pastoris* X33 strains were prepared, and the linearized pPIC3.5K-VP6-S-K88/K99 vectors and the competent cells were mixed and placed and then subjected to electrotransformation, and the bacterial solution after the electrotransformation was directly coated on a high concentration G418 antibiotic plate for screening.

Figure 2:
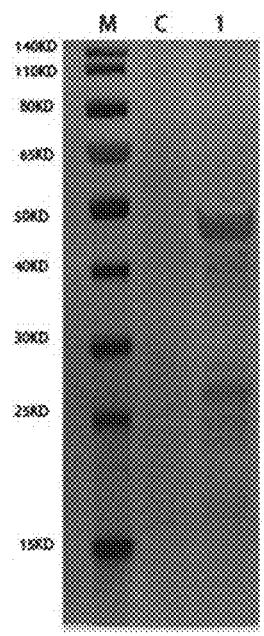
FIG. 2 shows Western blot detection result of VP6-S-K88/K99 fusion protein prepared in Example 1 of the present disclosure.

The monoclonal strains grown on the plates were subjected to shaking culture, amplification and expression, and fermented bacteria were crushed and subjected to SDS-PAGE detection and Western blot detection, the strains with positive detection results were *Pichia pastoris* X33-VP6-S-K88/K99 engineered bacteria that can express the VP6-S-K88/K99 fusion protein. The SDS-PAGE detection results are as shown in FIG. 1, and the Western blot detection results are as shown in FIG. 2, wherein C is a control group, and 1 is an experimental group.

The X33-VP6-S-K88/K99 engineered bacteria were activated in BMGY medium at 30° C. for 24 h; the activated culture bacterial solution was inoculated in BMGY medium at a ratio of 1:400 for fermentation, and cultured at 30° C. for 24 h, then changed into BMMY medium for continued induction of expression, and methanol was added once every 24 h so that the final concentration of methanol was 0.5%, and the bacteria were collected 72 h after induction of expression.

Example 2

Expression of Multilayer Chimeric VLP Particles by *Pichia pastoris* Expression System:

The genes encoding VP2-N93 protein were synthesized by means of genetic engineering, and the amino acid sequence was represented by SEQ ID NO: 10. The target genes were inserted into the pPICZ A vectors via Bst BI and Age I, and the positive recombinant vectors were screened out through enzymatic identification and sequencing, transformed into *E. Coli* DH5a competent cells for amplification, and the plasmids were extracted in large quantity, named as pPICZ A-VP2-N93.

After the pPICZ A-VP2-N93 plasmids were subjected to linearize restriction enzyme digestion with Pme I restriction endonuclease, the linear expression plasmids were recovered, and measured for the purity and concentration thereof.

The competent cells subjected to electrotransformation of *Pichia pastoris* X33-VP6-S-K88/K99 strains were prepared, and the linearized pPICZ A-VP2-N93 vectors and the competent cells were mixed and placed and then subjected to electrotransformation, and the bacterial solution after the electrotransformation was directly coated on a high concentration Zeocin antibiotic (2 mg/ml) plate for screening.

Figure 4:
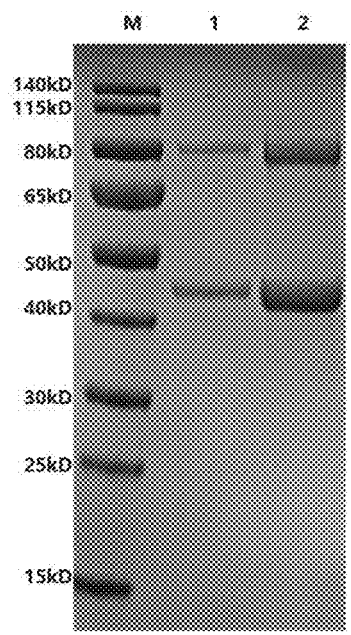
FIG. 4 shows the VP2-VP6 fusion protein prepared in Example 2.

The monoclonal strains grown on the plates were subjected to shaking culture, amplification and expression, and fermented bacteria were crushed and subjected to SDS-PAGE detection, the strains with positive detection results were *Pichia pastoris* X33-VP2-N93-VP6-S-K88/K99 engineered bacteria that can co-express the VP6-S-K88/K99 fusion protein and the VP2-N93 protein. The SDS-PAGE detection results are as shown in FIG. 4, where 1 and 2 are experimental groups of different concentrations.

The engineered bacteria were activated in BMGY medium at 30° C. for 24 h; the activated culture bacterial solution was inoculated in BMGY medium at a ratio of 1:400 for fermentation, and cultured at 30° C. for 24 h, then changed into BMMY medium for continued induction of expression, and methanol was added once every 24 h so that the final concentration of methanol was 0.5%, and the bacteria were collected 72 h after induction of expression.

Example 3

Purification of VP6-S-K88/K99 Fusion Protein and VP2-N93-VP6-S-K88/K99 Fusion Protein and Assembly of VLP:

Buffer A (20 mM HEPES, 300 mM NaCl, pH 7.3) was added to the thallus of the X33-VP6-S-K88/K99 engineered bacteria and the X33-VP2-N93-VP6-S-K88/K99 engineered bacteria in a mass volume ratio of 1:10, respectively, and the bacteria were crushed by a high pressure crushing method;

the crushed cells were centrifuged at 4° C., 12000 rpm for 60 min, after the supernatant from the centrifugation was precipitated with 30% ammonium sulfate at 4° C. for 1 h, the precipitate was resuspended again with buffer A for crude purification.

Figure 3:
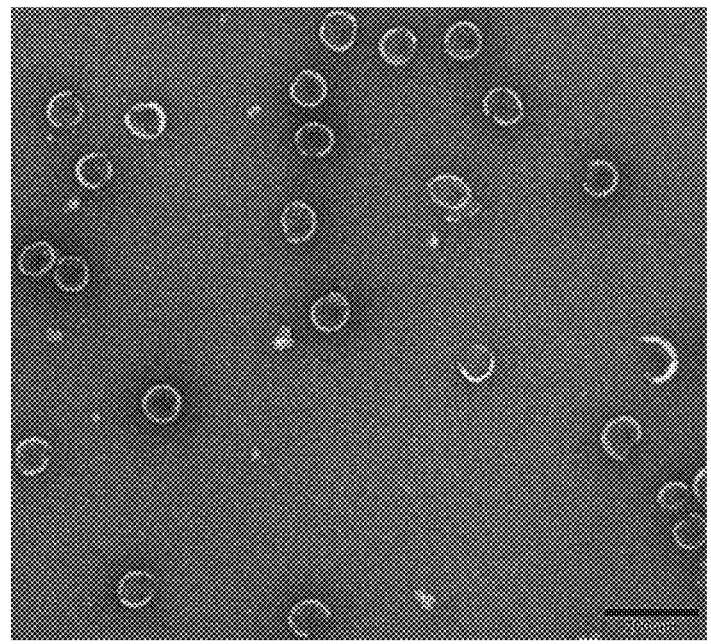
FIG. 3 is an electron micrograph of virus-like particles assembled from VP6-S-K88/K99 fusion protein.
Figure 5:
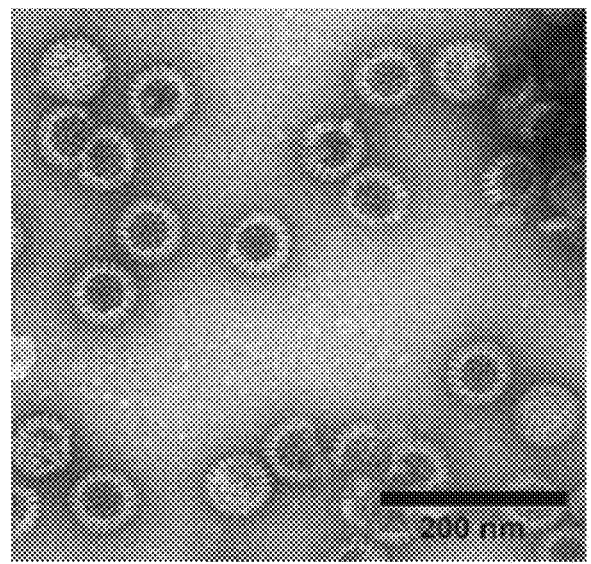
FIG. 5 is an electron micrograph of virus-like particles assembled from VP2-N93-VP6-S-K88/K99 fusion protein.
Figure 6:
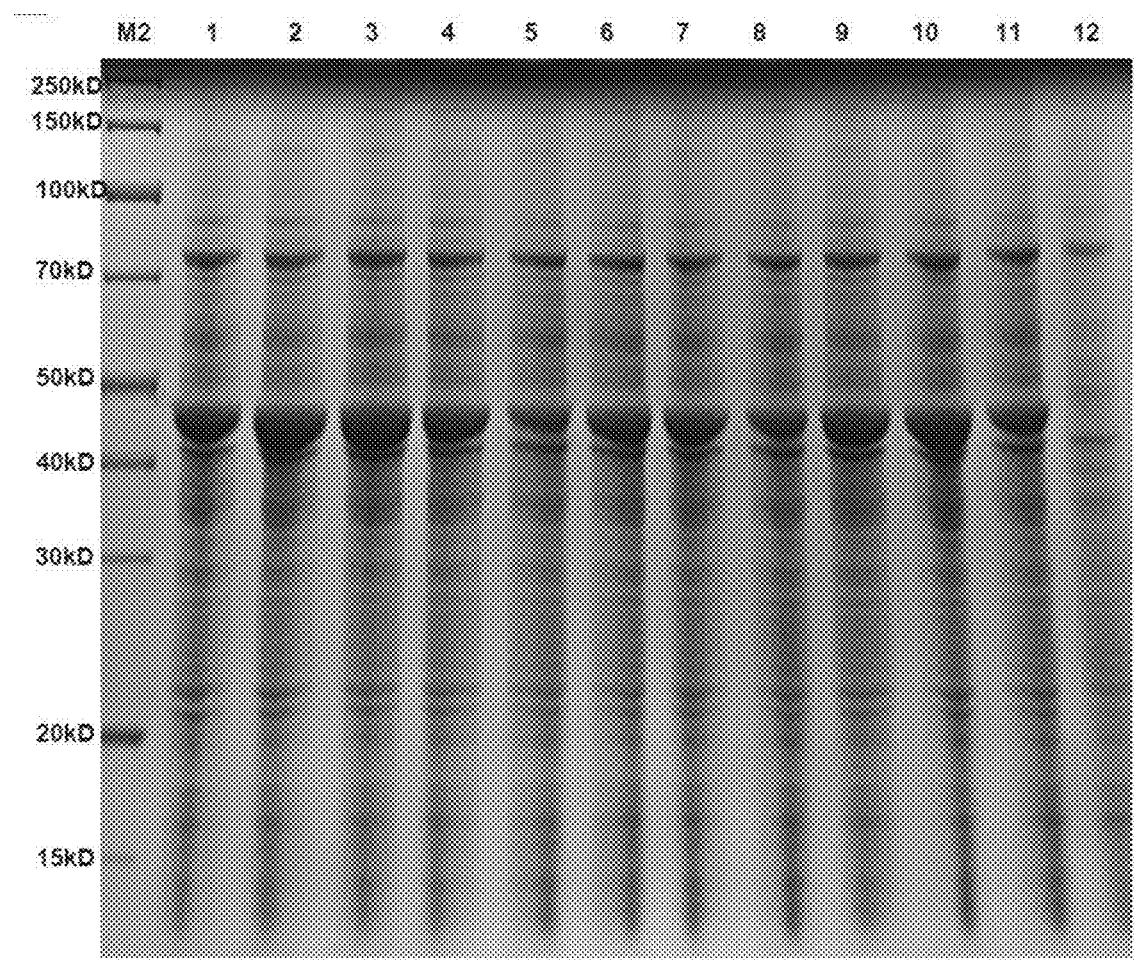
FIG. 6 shows SDS-PAGE detection result of VP6-S-K88/K99-test1 and VP6-S-K88/K99-test2 fusion proteins prepared in Example 4.
Figure 7:
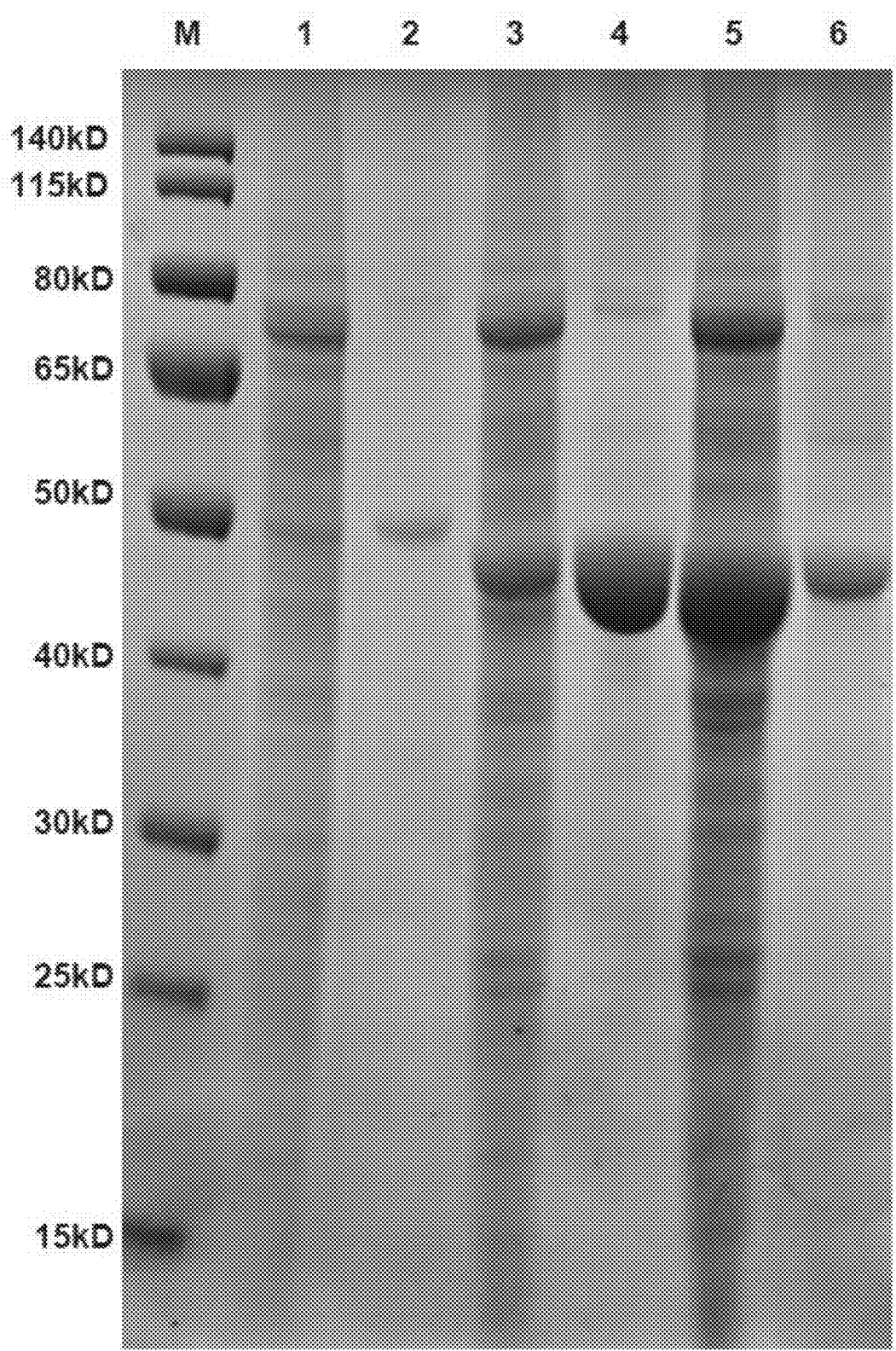
FIG. 7 shows SDS-PAGE detection result of lysis of X33-VP6-S-K88/K99-test1 engineering bacteria strain and X33-VP6-S-K88/K99-test2 engineering bacteria strain prepared in Example 4.
Figure 8:
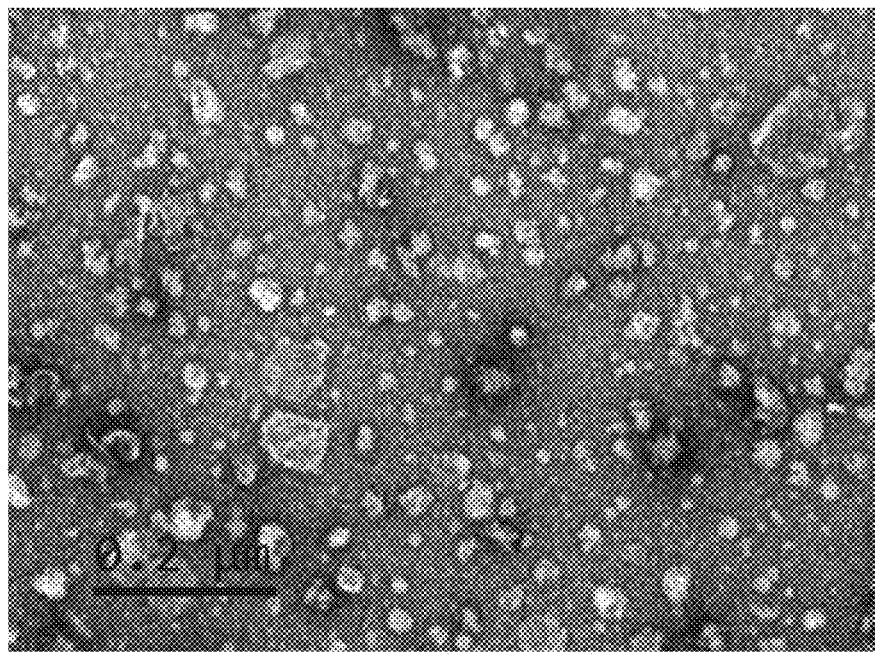
FIG. 8 is an electron micrograph of virus-like particles assembled from VP6-S-K88/K99-test2 fusion protein in Example 5.

The above purified target proteins were subjected to secondary purification by gel filtration chromatography, and the target proteins were collected. The VP6-S-K88/K99 target proteins were switched into buffer B (50 mM sodium citrate, 300 mM NaCl, pH 4.82) and then placed at 4° C. for assembly, and the particle size and uniformity thereof were detected with an electron microscope, and the results are as shown in FIG. 3. The particle size and uniformity of the VP2-N93-VP6-S-K88/K99 target proteins were detected with an electron microscope, and the results are as shown in FIG. 5.

Example 4

Expression of Fusion Protein by *Pichia pastoris* Expression System:

the bovine rotavirus VP6 protein structure was analyzed by means of structural biology, and the antigenic epitopes of the bovine coronavirus and pathogenic *E. coli* were embedded onto the bovine rotavirus VP6 protein backbones, wherein two sequences were designed, named as VP6-S-K88/K99-test1 and VP6-S-K88/K99-test2, respectively, and the specific amino acid sequences are represented by SEQ ID NO: 12 and SEQ ID NO: 13;

the fusion proteins VP6-S-K88/K99-test1 and VP6-S-K88/K99-test2 were subjected to *Pichia pastoris* expression system optimization, respectively, and the nucleotide sequences are represented by SEQ ID NO: 14 and SEQ ID NO: 15.

Genes encoding the VP6-S-K88/K99-test1 and VP6-S-K88/K99-test2 fusion proteins were synthesized by means of genetic engineering, the target genes were inserted into the pPIC3.5k vectors via Bam HI and Age I, and the positive recombinant vectors were screened out through enzymatic identification and sequencing, transformed into *E. Coli* DH5a competent cells for amplification, and the plasmids were extracted in large quantity, named as pPIC3.5K-VP6-S-K88/K99-test1 and pPIC3.5K-VP6-S-K88/K99-test2.

After the pPIC3.5K-VP6-S-K88/K99-test1, pPIC3.5K-VP6-S-K88/K99-test2 plasmids were subjected to linearized restriction enzyme digestion with Pme I restriction endonuclease, the linear expression plasmids were recovered, and measured for the purity and concentration thereof.

The competent cells subjected to electrotransformation of *Pichia pastoris* X33 strains were prepared, and the linearized pPIC3.5K-VP6-S-K88/K99-test1 and pPIC3.5K-VP6-S-K88/K99-test2 vectors and the competent cells were mixed and placed and then subjected to electrotransformation, and the bacterial solution after the electrotransformation was directly coated on a high concentration G418 antibiotic plate for screening.

The monoclonal strains grown on the plates were subjected to shaking culture, amplification and expression, and fermented bacteria were crushed and subjected to SDS-PAGE detection and Western blot detection, the strains with positive detection results were *Pichia pastoris* X33-VP6-S-K88/K99-test1 engineered bacteria that can express the VP6-S-K88/K99-test1 fusion protein and *Pichia pastoris* X33-VP6-S-K88/K99-test2 engineered bacteria that can express the VP6-S-K88/K99-test2 fusion protein. The SDS-PAGE detection results are as shown in FIG. 6, where 1-5 are experimental groups of VP6-S-K88/K99-test1, 6-11 are experimental groups of VP6-S-K88/K99-test2, and 12 is a control group.

The X33-VP6-S-K88/K99-test1 and X33-VP6-S-K88/K99-test2 engineered bacteria were activated in BMGY medium at 30° C. for 24 h; the activated culture bacterial solution was inoculated in BMGY medium at a ratio of 1:400 for fermentation, and cultured at 30° C. for 24 h, then changed into BMMY medium for continued induction of expression, and methanol was added once every 24 h so that the final concentration of methanol was 0.5%, and the bacteria were collected 72 h after induction of expression.

Example 5

Purification of VP6-S-K88/K99-Test1 Fusion Protein and VP6-S-K88/K99-Test2 Fusion Protein and Assembly of VLP:

Buffer A (20 mM HEPES, 300 mM NaCl, pH 7.3) was added to the thallus of the X33-VP6-S-K88/K99-test1 engineered bacteria and the X33-VP6-S-K88/K99-test2 engineered bacteria in a mass volume ratio of 1:10, respectively, and the bacteria were crushed by a high pressure crushing method;

the crushed cells were centrifuged at 4° C., 12000 rpm for 60 min, the supernatant from the centrifugation and the precipitate from the centrifugation were was subjected to SDS-PAGE identification, and SDS-PAGE detection results are as shown in FIG. 7, where 1 is the supernatant of the control group, 2 is the precipitate of the control group, 3 is the supernatant of the experimental group of VP6-S-K88/K99-test1, 4 is the precipitate of the experimental group of VP6-S-K88/K99-test1, 5 is the supernatant of the experimental group of VP6-S-K88/K99-test2, and 6 is the precipitate of the experimental group of VP6-S-K88/K99-test2.

In the above, the majority of VP6-S-K88/K99-test1 was present in insoluble form, which did not comply with the expectation, and no purification and electron microscopy experiments were performed.

In the above, the supernatant from centrifugation of VP6-S-K88/K99-test2 was first precipitated with 30% ammonium sulfate at 4° C. for 1 h, and the precipitate was resuspended again with buffer A for crude purification.

The above purified target proteins were subjected to secondary purification by gel filtration chromatography, and the target proteins were collected. The VP6-S-K88/K99-test2 target proteins were switched into buffer B (50 mM sodium citrate, 300 mM NaCl, pH 4.82) and then placed at 4° C. for assembly, and the particle size and uniformity thereof were detected with an electron microscope, and the results are as shown in FIG. 8.

Effect Example 1

Preparation of Calf Diarrhea Multivalent Vaccine and Antibody Evaluation:

Vaccine Preparation:

The VP6-S-K88/K99 VLP described above was diluted to different concentrations using PBS solution, and the diluted fusion protein solution and the SEPPIC ISA206 adjuvant were mixed together in a ratio of 1:1 of antigen component to adjuvant, and the final concentration was 100 μg/mL. The vaccine was subjected to aseptic inspection, viscosity measurement, and stability measurement according to the requirements of annexes of the Veterinary Pharmacopoeia of PRC (current edition), and then placed at 4° C. for later use.

Mouse Immunization:

6-week old female Balb/c mice were randomly grouped, 10 mice in each group and 2 groups in total, one group was not injected with vaccine (control group), and the other group was an experimental group, and injected with the prepared VLP vaccine at the dose of 0.1 mL per mouse (antigen protein content 10 μg). Two days before immunization, 100 μL of submaxillary blood was collected intravenously as a pre-immunization control. The blood collected was placed in a 1.5 mL EP tube, placed in a 37° C. water bath for 1 h, 4° C. for 2 h, 3000 rpm, centrifuged at 4° C. for 3 min, and the supernatant was separated and stored at −20° C. after partitioning. 21 days after the first time of immunization, 100 μL of blood was collected, and subjected to serum separation with the same method as the above; then secondary immunization was performed with an immunization dose of 0.1 mL per mouse (antigen protein content 10 μg). 14 days after the secondary immunization, 100 μL of blood was collected, and subjected to serum separation with the same method as the above.

Bovine Rotavirus Antibody Detection:

(1) Establishment of Bovine Rotavirus Detection Method

The separated bovine rotavirus was diluted with 50 mM phosphate buffer at pH 7.6 and then coated in the enzyme plate, 100 μL/well, 4° C. overnight. The next day the coating liquid was discarded, and the enzyme plate was washed 3 times with PBST, 200 μL/well. 2% bovine serum albumin (BSA) was added as blocking liquid, 100 μL/well, 37° C. 1 h. The blocking liquid was discarded, and after three times of washing, the negative and positive serum was diluted with 1% bovine serum albumin (BSA) in proportions and added to the enzyme plate, 100 μL/well, at 37° C. for 1 h. The liquid in the plate was discarded, and after five times of washing, HRP-labeled goat anti-bovine IgG diluted by 1% bovine serum albumin (BSA) at 1:2500 was added, 100 μL/well, at 37° C. for 1 h. The liquid in the plate was discarded, and after five times of washing, TMB developing solution was added, 100 μL/well, followed by light shielding color development at 37° C. for 15 min, and then 2 mol/L H2SO4 was added to terminate the reaction, 100 μL/well. The OD450 nm value was read on ELIASA.

(2) Bovine Rotavirus Antibody Detection 14 days after the secondary immunization of mice, antibody levels of all mice in the immunization group turned to be positive (S/N value>2.1), indicating that the vaccine prepared can induce the mice to generate anti-bovine rotavirus specific antibody, and the specific detection results are as shown in Table 1.

TABLE 1

| No. | Experimental Group (S/N value) | Control Group (S/N value) |
|---|---|---|
| 1 | 3.23 | 0.24 |
| 2 | 3.82 | 0.23 |
| 3 | 2.92 | 0.31 |
| 4 | 4.24 | 0.23 |
| 5 | 3.35 | 0.18 |
| 6 | 2.66 | 0.33 |
| 7 | 2.54 | 0.13 |
| 8 | 3.89 | 0.29 |
| 9 | 2.13 | 0.19 |
| 10 | 3.02 | 0.09 |

Mouse Challenging Experiments with E. coli K88, K99:

(1) Preparation of Bacterial Solution for Challenging

The challenging strains K88 and K99 used in the test were purchased from China institute for veterinary medicine, before challenging, the rejuvenated E. coli standard strains were respectively inoculated into conical flasks with 50 mL of LB liquid culture medium, and cultured at 37° C. for 16~20 hours under the condition of 200 rmp, and the concentration of the bacterial solution is $1 \times 10^8$ CFU/L. The bacterial solution was diluted by 1000 times with sterile LB liquid medium, two bacterial solutions were mixed in equal proportion, and stored at 4° C. for later use.

(2) Challenging

For the mice immunized above, 15 days after the secondary immunization, five mice in the control group were intraperitoneally injected with 0.2 mL of sterile normal saline; and the other five mice were intraperitoneally injected with 0.2 mL of the bacterial solution prepared above for challenging. The ten mice in the immunization experimental group were intraperitoneally injected with 0.2 mL of the bacterial solution for challenging. After challenging, the mice were observed every 3 hours, and the diarrhea, death and other conditions of the mice were recorded.

(3) Results 3 hours after the challenging, the challenged mice in the control group began to die, and 45 hours after the challenging, all of the five challenged mice in the control group died. For the mice injected with saline, all of the five mice survived 48 hours after injection. For the mice in the immunization group, nine mice survived and were healthy 48 hours after the challenging, and one mouse died of diarrhea 24 hours after challenging. The test results show that the protection rate of the prepared vaccine against pathogenic E. coli in the immunization group is 90%.

Finally, it should be noted that various examples above are merely used for illustrating the technical solutions of the present disclosure, rather than limiting the present disclosure. While the detailed description is made to the present disclosure with reference to the preceding examples, those ordinarily skilled in the art should understand that they still could modify the technical solutions recited in the preceding examples, or make equivalent substitutions to some or all of the technical features therein. These modifications or substitutions do not make the corresponding technical solutions essentially depart from the scope of the technical solutions of the various examples of the present disclosure.

What is claimed is:

1. A bovine rotavirus fusion protein, wherein the bovine rotavirus fusion protein contains a VP6 fragment, wherein the VP6 fragment comprises the amino acid sequence of SEQ ID NO: 8.

2. The bovine rotavirus fusion protein according to claim 1, wherein the bovine rotavirus fusion protein further contains a VP2 fragment.

3. A virus-like particle assembled from the bovine rotavirus fusion protein according to claim 1.

4. A method for preparing a virus-like particle, comprising expressing genes encoding the bovine rotavirus fusion protein that comprises SEQ ID NO: 8 in a host, wherein the host is yeast.

5. The method according to claim 4, further comprising screening the yeast by antibiotic selection pressure to obtain yeast that are monoclonal.

6. The method according to claim 4, wherein the method comprises inducing the yeast to express the bovine rotavirus fusion protein, lysing the yeast to extract supernatant, and then purifying the supernatant using an ammonium sulfate precipitation method and a chromatography method, so as to obtain the virus-like particle.

7. The bovine rotavirus fusion protein according to claim 1, wherein the bovine rotavirus fusion protein further contains a VP4 fragment.

8. The bovine rotavirus fusion protein according to claim 1, wherein the bovine rotavirus fusion protein further contains a VP7 fragment.

* * * * *

SEQUENCE LISTING

<160> NUMBER OF SEQ ID NOS: 15

<210> SEQ ID NO 1
<211> LENGTH: 10
<212> TYPE: PRT
<213> ORGANISM: Bovine Rotavirus

<400> SEQUENCE: 1

Arg Ser Gln Pro Ala His Asp Asn Leu Met
1               5                   10

<210> SEQ ID NO 2
<211> LENGTH: 12
<212> TYPE: PRT
<213> ORGANISM: Bovine Rotavirus

<400> SEQUENCE: 2

Asp Tyr Ser Cys Ala Ile Asn Ala Pro Ala Asn Thr
1               5                   10

<210> SEQ ID NO 3
<211> LENGTH: 21
<212> TYPE: PRT
<213> ORGANISM: Bovine Rotavirus

```
<400> SEQUENCE: 3

Arg Pro Pro Asn Met Thr Pro Ala Val Ala Ala Leu Phe Pro Asn Ala
1               5                   10                  15

Gln Pro Phe Glu His
            20

<210> SEQ ID NO 4
<211> LENGTH: 397
<212> TYPE: PRT
<213> ORGANISM: Bovine Rotavirus

<400> SEQUENCE: 4

Met Asp Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Leu Ile Thr Met Asn Gly Asn Glu Phe Gln Thr
        35                  40                  45

Gly Gly Ile Gly Asn Leu Pro Ile Arg Asn Trp Asn Phe Asp Phe Gly
    50                  55                  60

Leu Leu Gly Thr Thr Leu Leu Asn Leu Asp Ala Asn Tyr Val Glu Thr
65                  70                  75                  80

Ala Arg Asn Thr Ile Asp Tyr Phe Val Asp Phe Val Asp Asn Val Cys
                85                  90                  95

Met Asp Glu Met Val Arg Glu Ser Gln Arg Asn Gly Ile Ala Pro Gln
            100                 105                 110

Ser Asp Ser Leu Arg Lys Leu Ser Gly Ile Lys Phe Lys Gly Ile Asn
        115                 120                 125

Phe Asp Asn Ser Ser Glu Tyr Ile Glu Asn Trp Asn Leu Gln Asn Arg
    130                 135                 140

Arg Gln Arg Thr Gly Phe Thr Phe His Lys Pro Asn Ile Phe Pro Tyr
145                 150                 155                 160

Ser Ala Ser Phe Thr Leu Asn Arg Ser Gln Pro Ala His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Thr Gln Gln Phe
        195                 200                 205

Glu His Ile Val Gln Leu Arg Arg Val Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Tyr Phe Asn Pro Val Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Ile Ala Arg Asn Phe Asp Thr Ile
        275                 280                 285

Arg Leu Ser Phe Gln Leu Met Arg Pro Pro Asn Met Thr Pro Ala Val
    290                 295                 300

Ala Ala Leu Phe Pro Asn Ala Gln Pro Phe Glu His His Ala Thr Ile
305                 310                 315                 320

Gly Leu Thr Leu Arg Ile Glu Ser Ala Val Cys Glu Ser Val Leu Ala
                325                 330                 335
```

```
Asp Ala Ser Glu Thr Met Leu Ala Asn Val Thr Ser Val Arg Gln Glu
                340                 345                 350

Tyr Ala Ile Pro Val Gly Pro Val Phe Pro Pro Gly Met Asn Trp Thr
            355                 360                 365

Asp Leu Ile Thr Asn Tyr Ser Pro Ser Arg Glu Asp Asn Leu Gln Arg
        370                 375                 380

Val Phe Thr Val Ala Ser Ile Arg Ser Met Leu Val Lys
385                 390                 395

<210> SEQ ID NO 5
<211> LENGTH: 14
<212> TYPE: PRT
<213> ORGANISM: Bovine Coronavirus

<400> SEQUENCE: 5

Thr Thr Gly Tyr Arg Phe Thr Asn Phe Glu Pro Phe Thr Val
1               5                   10

<210> SEQ ID NO 6
<211> LENGTH: 10
<212> TYPE: PRT
<213> ORGANISM: Escherichia coli

<400> SEQUENCE: 6

Asn Pro Asp Gly Glu Thr Asn Lys Lys Gly
1               5                   10

<210> SEQ ID NO 7
<211> LENGTH: 10
<212> TYPE: PRT
<213> ORGANISM: Escherichia coli

<400> SEQUENCE: 7

Lys Asp Asp Arg Ala Pro Ser Asn Gly Gly
1               5                   10

<210> SEQ ID NO 8
<211> LENGTH: 388
<212> TYPE: PRT
<213> ORGANISM: Artificial Sequence
<220> FEATURE:
<223> OTHER INFORMATION: VP6-S-K88/K99, derived form bovine rotavirus,
      bovine coronavirus and E. coli

<400> SEQUENCE: 8

Met Asp Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Leu Ile Thr Met Asn Gly Asn Glu Phe Gln Thr
        35                  40                  45

Gly Gly Ile Gly Asn Leu Pro Ile Arg Asn Trp Asn Phe Asp Phe Gly
    50                  55                  60

Leu Leu Gly Thr Thr Leu Leu Asn Leu Asp Ala Asn Tyr Val Glu Thr
65                  70                  75                  80

Ala Arg Asn Thr Ile Asp Tyr Phe Val Asp Phe Val Asp Asn Val Cys
                85                  90                  95

Met Asp Glu Met Val Arg Glu Ser Gln Arg Asn Gly Ile Ala Pro Gln
            100                 105                 110

Ser Asp Ser Leu Arg Lys Leu Ser Gly Ile Lys Phe Lys Gly Ile Asn
        115                 120                 125
```

```
Phe Asp Asn Ser Ser Glu Tyr Ile Glu Asn Trp Asn Leu Gln Asn Arg
        130                 135                 140

Arg Gln Arg Thr Gly Phe Thr Phe His Lys Pro Asn Ile Phe Pro Tyr
145                 150                 155                 160

Ser Ala Ser Phe Thr Leu Asn Asn Pro Asp Gly Glu Thr Asn Lys Lys
                165                 170                 175

Gly Gly Thr Met Trp Leu Asn Ala Gly Ser Glu Ile Gln Val Ala Gly
                180                 185                 190

Phe Lys Asp Asp Arg Ala Pro Ser Asn Gly Gly Gln Gln Phe Glu His
                195                 200                 205

Ile Val Gln Leu Arg Arg Val Leu Thr Thr Ala Thr Ile Thr Leu Leu
        210                 215                 220

Pro Asp Ala Glu Arg Phe Ser Phe Pro Arg Val Ile Asn Ser Ala Asp
225                 230                 235                 240

Gly Ala Thr Thr Trp Tyr Phe Asn Pro Val Ile Leu Arg Pro Asn Asn
                245                 250                 255

Val Glu Val Glu Phe Leu Leu Asn Gly Gln Ile Ile Asn Thr Tyr Gln
                260                 265                 270

Ala Arg Phe Gly Thr Ile Ile Ala Arg Asn Phe Asp Thr Ile Arg Leu
                275                 280                 285

Ser Phe Gln Leu Met Thr Thr Gly Tyr Arg Phe Thr Asn Phe Glu Pro
        290                 295                 300

Phe Thr Val His Ala Thr Ile Gly Leu Thr Leu Arg Ile Glu Ser Ala
305                 310                 315                 320

Val Cys Glu Ser Val Leu Ala Asp Ala Ser Glu Thr Met Leu Ala Asn
                325                 330                 335

Val Thr Ser Val Arg Gln Glu Tyr Ala Ile Pro Val Gly Pro Val Phe
                340                 345                 350

Pro Pro Gly Met Asn Trp Thr Asp Leu Ile Thr Asn Tyr Ser Pro Ser
                355                 360                 365

Arg Glu Asp Asn Leu Gln Arg Val Phe Thr Val Ala Ser Ile Arg Ser
        370                 375                 380

Met Leu Val Lys
385

<210> SEQ ID NO 9
<211> LENGTH: 1188
<212> TYPE: DNA
<213> ORGANISM: Artificial Sequence
<220> FEATURE:
<223> OTHER INFORMATION: nucleotide sequence encoding VP6-S-K88/K99,
      derived form bovine rotavirus, bovine coronavirus and E. coli

<400> SEQUENCE: 9
atggatgttt tatactcttt gtcaaaaact ttgaaagatg ctagagataa gattgtcgag      60
ggcacactgt attccaacgt ttcagacctt attcaacagt tcaaccaaat gttaatcacg     120
atgaacggca acgagtttca aaccggcggt atcgtaatc tacctattag gaactggaac     180
tttgatttcg gtttgcttgg cacaacgttg ttgaatctgg atgccaatta tgtggaaact     240
gctcgtaata cgatagatta ttttgttgat tttgtggata cgtatgcat ggatgaaatg     300 gtcagggagt cacagaggaa cggtattgct ccacaatctg actctcttcg taaacttagt     360
ggcataaagt tcaaaggaat caacttcgat aattcatccg aatatattga gaactggaac     420
ctgcagaata gaaggcaaag gacaggtttt acgtttcaca agccaaacat ttttccctac     480
tccgcttcat ttaccctgaa taatccagac ggagaaacga acaagaaggg tggtacaatg     540
```

```
tggctaaacg ccggttcaga gattcaagtc gcaggcttta aggacgacag agccccctcc      600
aacggcggac aacagttcga acacatagtt caactacgta gagtgcttac gactgctacg      660
attaccctgc tgcccgacgc tgaaaggttc tctttccctc gtgtcataaa cagtgcagat      720
ggtgctacca cgtggtactt taaccccgtt atactgcgtc ccaacaatgt cgaggtcgag      780
ttcctactaa acggtcagat cattaatacg taccaagcca ggtttggcac tataatagca      840
cgtaatttcg atactattag actgtctttt cagctaatgg gtggctccac taccggctac      900
cgttttacta attttgagcc tttcacagtc ggcggaggct cacatgcaac catcggtcta      960
accctaagga tcgaatctgc agtctgcgaa tcagtgctag ctgatgcttc agagactatg     1020
ctagccaacg taaccagtgt acgtcaggaa tatgcaattc ccgttggccc agtgtttcca     1080
cctggtatga actggactga cctgatcact aactattctc ctagtaggga ggataactta     1140
caaagagtct tcaccgtagc cagtattcgt agtatgttgg ttaaataa                  1188
```

<210> SEQ ID NO 10
<211> LENGTH: 788
<212> TYPE: PRT
<213> ORGANISM: Artificial Sequence
<220> FEATURE:
<223> OTHER INFORMATION: VP2-N93 protein,derived form bovine rotavirus

<400> SEQUENCE: 10

```
Lys Thr Ile Pro Thr Phe Glu Pro Lys Glu Ser Ile Leu Lys Lys Leu
1               5                   10                  15

Glu Asp Ile Arg Pro Glu Gln Ala Lys Lys Gln Thr Lys Leu Phe Arg
            20                  25                  30

Ile Phe Glu Pro Arg Gln Leu Pro Ile Tyr Arg Ala Asn Gly Glu Lys
        35                  40                  45

Glu Leu Arg Asn Arg Trp Tyr Trp Lys Leu Lys Lys Asp Thr Leu Pro
    50                  55                  60

Asp Gly Asp Tyr Asp Val Arg Glu Tyr Phe Leu Asn Leu Tyr Asp Gln
65                  70                  75                  80

Val Leu Thr Glu Met Pro Asp Tyr Leu Leu Leu Lys Asp Met Ala Val
                85                  90                  95

Glu Asn Lys Asn Ser Arg Asp Ala Gly Lys Val Val Asp Ser Glu Thr
            100                 105                 110

Ala Ser Ile Cys Asp Ala Ile Phe Gln Asp Glu Glu Thr Glu Gly Ala
        115                 120                 125

Val Arg Arg Phe Ile Ala Glu Met Arg Gln Arg Val Gln Ala Asp Arg
    130                 135                 140

Asn Val Val Asn Tyr Pro Ser Ile Leu His Pro Ile Asp Tyr Ala Phe
145                 150                 155                 160

Asn Glu Tyr Phe Leu Gln His Gln Leu Val Glu Pro Leu Asn Asn Asp
                165                 170                 175

Ile Ile Phe Asn Tyr Ile Pro Glu Arg Ile Arg Asn Asp Val Asn Tyr
            180                 185                 190

Ile Leu Asn Met Asp Arg Asn Leu Pro Ser Thr Ala Arg Tyr Ile Arg
        195                 200                 205

Pro Asn Leu Leu Gln Asp Arg Leu Asn Leu His Asp Asn Phe Glu Ser
    210                 215                 220

Leu Trp Asp Thr Ile Thr Thr Ser Asn Tyr Ile Leu Ala Arg Ser Val
225                 230                 235                 240

Val Pro Asp Leu Lys Glu Leu Val Ser Thr Glu Ala Gln Ile Gln Lys
                245                 250                 255
```

-continued

```
Met Ser Gln Asp Leu Gln Leu Glu Ala Leu Thr Ile Gln Ser Glu Thr
            260                 265                 270

Gln Phe Leu Thr Gly Ile Asn Ser Gln Ala Ala Asn Asp Cys Phe Lys
        275                 280                 285

Thr Leu Ile Ala Ala Met Leu Ser Gln Arg Thr Met Ser Leu Asp Phe
    290                 295                 300

Val Thr Thr Asn Tyr Met Ser Leu Ile Ser Gly Met Trp Leu Leu Thr
305                 310                 315                 320

Val Val Pro Asn Asp Met Phe Ile Arg Glu Ser Leu Val Ala Cys Gln
                325                 330                 335

Leu Ala Ile Val Asn Thr Ile Ile Tyr Pro Ala Phe Gly Met Gln Arg
            340                 345                 350

Met His Tyr Arg Asn Gly Asp Pro Gln Thr Pro Phe Gln Ile Ala Glu
        355                 360                 365

Gln Gln Ile Gln Asn Phe Gln Val Ala Asn Trp Leu His Phe Val Asn
    370                 375                 380

His Asn Gln Phe Arg Gln Val Val Ile Asp Gly Val Leu Asn Gln Val
385                 390                 395                 400

Leu Asn Asp Asn Ile Arg Asn Gly His Val Ile Asn Gln Leu Met Glu
                405                 410                 415

Ala Leu Met Gln Leu Ser Arg Gln Gln Phe Pro Thr Met Pro Val Asp
            420                 425                 430

Tyr Lys Arg Ser Ile Gln Arg Gly Ile Leu Leu Leu Ser Asn Arg Leu
        435                 440                 445

Gly Gln Leu Val Asp Leu Thr Arg Leu Leu Ala Tyr Asn Tyr Glu Thr
    450                 455                 460

Leu Met Ala Cys Val Thr Met Asn Met Gln His Val Gln Thr Leu Thr
465                 470                 475                 480

Thr Glu Lys Leu Gln Leu Thr Ser Val Ser Ser Leu Cys Met Leu Ile
                485                 490                 495

Gly Asn Ala Thr Val Ile Pro Ser Pro Gln Thr Leu Phe His Tyr Tyr
            500                 505                 510

Asn Val Asn Val Asn Phe His Ser Asn Tyr Asn Glu Arg Ile Asn Asp
        515                 520                 525

Ala Val Ala Ile Ile Thr Ala Ala Asn Arg Leu Asn Leu Tyr Gln Lys
    530                 535                 540

Lys Met Lys Ala Ile Val Glu Asp Phe Leu Lys Arg Leu His Ile Phe
545                 550                 555                 560

Asp Val Ala Arg Val Pro Asp Asp Gln Met Tyr Arg Leu Arg Asp Arg
                565                 570                 575

Leu Arg Leu Leu Pro Val Glu Val Arg Arg Leu Asp Ile Phe Asn Leu
            580                 585                 590

Ile Leu Met Asn Met Asp Gln Ile Glu Arg Ala Ser Asp Lys Ile Ala
        595                 600                 605

Gln Gly Val Ile Ile Ala Tyr Arg Asp Met Gln Leu Glu Arg Asp Glu
    610                 615                 620

Met Tyr Gly Tyr Val Asn Ile Ala Arg Asn Leu Asp Gly Phe Gln Gln
625                 630                 635                 640

Ile Asn Leu Glu Glu Leu Met Arg Thr Gly Asp Tyr Ala Gln Ile Thr
                645                 650                 655

Asn Met Leu Leu Asn Asn Gln Pro Val Ala Leu Val Gly Ala Leu Pro
            660                 665                 670
```

```
Phe Val Thr Asp Ser Ser Val Ile Ser Leu Ile Ala Lys Leu Asp Ala
            675                 680                 685

Thr Val Phe Ala Gln Ile Val Lys Leu Arg Lys Val Asp Thr Leu Arg
    690                 695                 700

Pro Ile Leu Tyr Lys Ile Asn Ser Asp Ser Asn Asp Phe Tyr Leu Val
705                 710                 715                 720

Ala Asn Tyr Asp Trp Val Pro Thr Ser Thr Lys Val Tyr Lys Gln
                725                 730                 735

Val Pro Gln Gln Phe Asp Phe Arg Asn Ser Met His Met Leu Ala Ser
            740                 745                 750

Asn Leu Thr Phe Thr Val Tyr Ser Asp Leu Leu Ala Phe Val Ser Ala
            755                 760                 765

Asp Thr Val Glu Pro Ile Asn Ala Val Ala Phe Asp Asn Met Arg Ile
    770                 775                 780

Met Asn Glu Leu
785

<210> SEQ ID NO 11
<211> LENGTH: 21
<212> TYPE: PRT
<213> ORGANISM: Bovine Coronavirus

<400> SEQUENCE: 11

Gly Gly Ser Thr Thr Gly Tyr Arg Phe Thr Asn Phe Glu Pro Phe Thr
1               5                   10                  15

Val Gly Gly Gly Ser
            20

<210> SEQ ID NO 12
<211> LENGTH: 395
<212> TYPE: PRT
<213> ORGANISM: Artificial Sequence
<220> FEATURE:
<223> OTHER INFORMATION: VP6-S-K88/K99-test1,derived form bovine
      rotavirus, bovine coronavirus and E. coli

<400> SEQUENCE: 12

Met Asp Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Leu Ile Thr Met Asn Gly Asn Glu Phe Gln Thr
        35                  40                  45

Gly Gly Ile Gly Asn Leu Pro Ile Arg Asn Trp Asn Phe Asp Phe Gly
    50                  55                  60

Leu Leu Gly Thr Thr Leu Leu Asn Leu Asp Ala Asn Tyr Val Glu Thr
65                  70                  75                  80

Ala Arg Asn Thr Ile Asp Tyr Phe Val Asp Phe Val Asp Asn Val Cys
                85                  90                  95

Met Asp Glu Met Val Arg Glu Ser Gln Arg Asn Gly Ile Ala Pro Gln
            100                 105                 110

Ser Asp Ser Leu Arg Lys Leu Ser Gly Ile Lys Phe Lys Gly Ile Asn
        115                 120                 125

Phe Asp Asn Ser Ser Glu Tyr Ile Glu Asn Trp Asn Leu Gln Asn Arg
    130                 135                 140

Arg Gln Arg Thr Gly Phe Thr Phe His Lys Pro Asn Ile Phe Pro Tyr
145                 150                 155                 160
```

```
Ser Ala Ser Phe Thr Leu Asn Gly Gly Ser Thr Thr Gly Tyr Arg Phe
            165                 170                 175

Thr Asn Phe Glu Pro Phe Thr Val Gly Gly Ser Gly Thr Met Trp
        180                 185                 190

Leu Asn Ala Gly Ser Glu Ile Gln Val Ala Gly Phe Asn Pro Asp Gly
            195                 200                 205

Glu Thr Asn Lys Lys Gly Gln Gln Phe Glu His Ile Val Gln Leu Arg
        210                 215                 220

Arg Val Leu Thr Thr Ala Thr Ile Thr Leu Leu Pro Asp Ala Glu Arg
225                 230                 235                 240

Phe Ser Phe Pro Arg Val Ile Asn Ser Ala Asp Gly Ala Thr Thr Trp
                245                 250                 255

Tyr Phe Asn Pro Val Ile Leu Arg Pro Asn Asn Val Glu Val Glu Phe
            260                 265                 270

Leu Leu Asn Gly Gln Ile Ile Asn Thr Tyr Gln Ala Arg Phe Gly Thr
            275                 280                 285

Ile Ile Ala Arg Asn Phe Asp Thr Ile Arg Leu Ser Phe Gln Leu Met
        290                 295                 300

Lys Asp Asp Arg Ala Pro Ser Asn Gly Gly His Ala Thr Ile Gly Leu
305                 310                 315                 320

Thr Leu Arg Ile Glu Ser Ala Val Cys Glu Ser Val Leu Ala Asp Ala
                325                 330                 335

Ser Glu Thr Met Leu Ala Asn Val Thr Ser Val Arg Gln Glu Tyr Ala
            340                 345                 350

Ile Pro Val Gly Pro Val Phe Pro Pro Gly Met Asn Trp Thr Asp Leu
        355                 360                 365

Ile Thr Asn Tyr Ser Pro Ser Arg Glu Asp Asn Leu Gln Arg Val Phe
        370                 375                 380

Thr Val Ala Ser Ile Arg Ser Met Leu Val Lys
385                 390                 395

<210> SEQ ID NO 13
<211> LENGTH: 395
<212> TYPE: PRT
<213> ORGANISM: Artificial Sequence
<220> FEATURE:
<223> OTHER INFORMATION: VP6-S-K88/K99-test2,derived form bovine
      rotavirus, bovine coronavirus and E. coli

<400> SEQUENCE: 13

Met Asp Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Leu Ile Thr Met Asn Gly Asn Glu Phe Gln Thr
        35                  40                  45

Gly Gly Ile Gly Asn Leu Pro Ile Arg Asn Trp Asn Phe Asp Phe Gly
    50                  55                  60

Leu Leu Gly Thr Thr Leu Leu Asn Leu Asp Ala Asn Tyr Val Glu Thr
65                  70                  75                  80

Ala Arg Asn Thr Ile Asp Tyr Phe Val Asp Phe Val Asp Asn Val Cys
                85                  90                  95

Met Asp Glu Met Val Arg Glu Ser Gln Arg Asn Gly Ile Ala Pro Gln
            100                 105                 110
```

```
Ser Asp Ser Leu Arg Lys Leu Ser Gly Ile Lys Phe Lys Gly Ile Asn
            115                 120                 125
Phe Asp Asn Ser Ser Glu Tyr Ile Glu Asn Trp Asn Leu Gln Asn Arg
        130                 135                 140
Arg Gln Arg Thr Gly Phe Thr Phe His Lys Pro Asn Ile Phe Pro Tyr
145                 150                 155                 160
Ser Ala Ser Phe Thr Leu Asn Lys Asp Asp Arg Ala Pro Ser Asn Gly
                165                 170                 175
Gly Gly Thr Met Trp Leu Asn Ala Gly Ser Glu Ile Gln Val Ala Gly
            180                 185                 190
Phe Asn Pro Asp Gly Glu Thr Asn Lys Lys Gly Gln Gln Phe Glu His
        195                 200                 205
Ile Val Gln Leu Arg Arg Val Leu Thr Thr Ala Thr Ile Thr Leu Leu
    210                 215                 220
Pro Asp Ala Glu Arg Phe Ser Phe Pro Arg Val Ile Asn Ser Ala Asp
225                 230                 235                 240
Gly Ala Thr Thr Trp Tyr Phe Asn Pro Val Ile Leu Arg Pro Asn Asn
                245                 250                 255
Val Glu Val Glu Phe Leu Leu Asn Gly Gln Ile Ile Asn Thr Tyr Gln
            260                 265                 270
Ala Arg Phe Gly Thr Ile Ile Ala Arg Asn Phe Asp Thr Ile Arg Leu
        275                 280                 285
Ser Phe Gln Leu Met Gly Gly Ser Thr Thr Gly Tyr Arg Phe Thr Asn
    290                 295                 300
Phe Glu Pro Phe Thr Val Gly Gly Gly Ser His Ala Thr Ile Gly Leu
305                 310                 315                 320
Thr Leu Arg Ile Glu Ser Ala Val Cys Glu Ser Val Leu Ala Asp Ala
                325                 330                 335
Ser Glu Thr Met Leu Ala Asn Val Thr Ser Val Arg Gln Glu Tyr Ala
            340                 345                 350
Ile Pro Val Gly Pro Val Phe Pro Pro Gly Met Asn Trp Thr Asp Leu
        355                 360                 365
Ile Thr Asn Tyr Ser Pro Ser Arg Glu Asp Asn Leu Gln Arg Val Phe
    370                 375                 380
Thr Val Ala Ser Ile Arg Ser Met Leu Val Lys
385                 390                 395

<210> SEQ ID NO 14
<211> LENGTH: 1185
<212> TYPE: DNA
<213> ORGANISM: Artificial Sequence
<220> FEATURE:
<223> OTHER INFORMATION: nucleotide sequence encoding VP6-S-K88/K99-
      test1, derived form bovine rotavirus, bovine coronavirus and E.
      coli

<400> SEQUENCE: 14
atggatgtac tgtactcatt gagtaaaaca cttaaggacg ccagggataa gatagtggaa      60
ggtaccctgt attcaaatgt gtctgatttg atacaacaat ttaatcaaat gctaataaca     120
atgaatggca acgaattcca gaccggtgga attggaaacc tacctataag gaactggaat     180
ttcgatttcg gccttttggg tacaacgctg ctaaacctag atgccaacta tgtcgaaacg     240
gcaagaaata caatagatta ttttgtggac tttgttgaca acgtgtgcat ggatgagatg     300
gtgagagagt cccagaggaa tggtatcgct ccacaatcag atagtctgag aaagctgtct     360
ggtataaaat tcaagggcat taacttcgac aattcaagtg aatacatcga gaactggaat     420
```

| | |
|---|---:|
| ctgcagaatc gtaggcaacg tacgggattc acattccata agcccaacat cttcccatat | 480 |
| tcagctagtt tcacacttaa cggaggctcc actacgggtt atcgtttcac gaactttgaa | 540 |
| cctttcacgg tgggtggcgg atcaggtact atgtggttaa acgctggatc agaaatacaa | 600 |
| gtagcaggct ttaatcccga cggagagact aacaagaaag gccaacaatt cgaacatata | 660 |
| gttcagttac gtagagttct acaacagct actataactc tattacctga cgccgagcgt | 720 |
| ttcagtttcc ccagagtaat taacagtgct gacggagcaa ctacttggta ttttaacccc | 780 |
| gttattctaa ggccaaacaa tgtggaggta gagtttcttc taaatggtca aatcatcaac | 840 |
| acgtaccagg ccagattcgg tactataatt gcaagaaact cgatacgat aaggctatca | 900 |
| tttcagctga tgaaggacga cagggctccc tctaacggcg gtcacgctac catcggactt | 960 |
| accctaagga tcgaatccgc tgtgtgtgag tccgttcttg cagatgcttc agagacgatg | 1020 |
| ctggctaatg taacttccgt cagacaagaa tatgctattc cagttggtcc cgttttcccc | 1080 |
| cccggaatga actggacgga cctgataaca aattattcac caagtagaga ggacaatcta | 1140 |
| caaagggtct ttaccgttgc atccataagg tccatgctag taaaa | 1185 |

<210> SEQ ID NO 15
<211> LENGTH: 1185
<212> TYPE: DNA
<213> ORGANISM: Artificial Sequence
<220> FEATURE:
<223> OTHER INFORMATION: nucleotide sequence encoding VP6-S-K88/K99-
test2, derived form bovine rotavirus, bovine coronavirus and E.
coli

<400> SEQUENCE: 15

| | |
|---|---:|
| atggacgttc tgtactcctt gtctaaaact ctgaaggacg caagggataa gatcgtagaa | 60 |
| ggtacattat attcaaatgt gtccgatttg attcaacagt tcaatcaaat gttgattacg | 120 |
| atgaatggta atgagttcca acaggagga atcggtaatt tgcctatccg taactggaat | 180 |
| ttcgactttg gcttgcttgg tactacccct ctaaacttgg atgcaaacta tgtcgaaacg | 240 |
| gcaaggaata cgatcgacta cttcgttgat ttcgttgata atgtttgtat ggatgagatg | 300 |
| gtgagggaat ctcaacgtaa tggcattgct ccccaatctg acagtctgag aaagttgtct | 360 |
| ggtatcaagt ttaaaggcat aaactttgac aactcttccg agtacataga gaattggaac | 420 |
| ttgcagaata ggcgtcagag gactggcttt actttccata aaccaaacat attcccttat | 480 |
| tccgcctcat tcacgctgaa taaggacgac agggccccca gtaatggagg cggtacaatg | 540 |
| tggctaaacg caggatcaga gatccaggtc gcaggcttta atcccgatgg tgagactaat | 600 |
| aaaaaggac aacaattcga acatatagta caactgagac gtgtgctgac tacagctacc | 660 |
| ataaccctt tgcccgatgc tgagagattc tctttcccaa gggttattaa ctccgccgac | 720 |
| ggagccacca cgtggtactt caatccagtt atccttaggc ctaacaacgt tgaggttgaa | 780 |
| ttcttgttaa acgacaaat catcaatacc tatcaggctc gtttcggtac tatcatagca | 840 |
| cgtaacttcg atactatcag acttagtttc cagctgatgg tggttccac tacgggttac | 900 |
| cgttttacta atttcgagcc ttttacagta ggaggcggct cccacgctac cattggtcta | 960 |
| acgttgcgta tagaaagtgc tgtatgtgag tctgttttgg ccgatgcttc gaaacaatg | 1020 |
| ttggcaaatg taacttccgt aagacaagaa tacgctatac ctgttggacc tgttttccct | 1080 |
| cctggcatga actggaccga cttgatcacg aattactccc ccagtagaga agacaatttg | 1140 |
| caaagagtct tcaccgtagc tagtatccgt tcaatgctag ttaaa | 1185 |